US00PP16154P3

(12) United States Plant Patent
Carruth

(10) Patent No.: US PP16,154 P3
(45) Date of Patent: Dec. 13, 2005

(54) CLIMBING ROSE PLANT NAMED 'WEKWESFLUT'

(50) Latin Name: ***Rosa* sp.**
Varietal Denomination: WEKwesflut

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 289 days.

(21) Appl. No.: 10/306,926

(22) Filed: Nov. 29, 2002

(65) Prior Publication Data

US 2004/0107468 P1 Jun. 3, 2004

(51) Int. Cl.[7] ..... A01H 5/00
(52) U.S. Cl. ..... Plt./109
(58) Field of Search ..... Plt./109, 111, 112

*Primary Examiner*—Kent Bell
(74) *Attorney, Agent, or Firm*—Christie, Parker & Hale, LLP

(57) ABSTRACT

A new variety of Climbing rose suitable for garden decoration, having flowers of apricot orange coloration with a yellow reverse.

1 Drawing Sheet

Botanical classification: *Rosa* sp.
Varietal name: 'WEKwesflut'.

BACKGROUND OF THE INVENTION

This invention relates to a new and distinct variety of Climbing Rose. The varietal denomination of the new variety is 'WEKwesflut'. It has as its seed parent the variety known as 'KORwest' (not patented) and as its pollen parent the variety known as 'WEKplasol' (U.S. Plant Pat. No. 9,715).

SUMMARY OF THE INVENTION

Among the features which distinguish the new variety from other presently available and commercial rose cultivars known to the inventor are the following combination of characteristics: its peduncle with numerous stipitate glands bearing the sweet juniper fragrance of moss roses, its strong spicy fragrance of the flower, its intense red suffusion on the peduncle, bud and the new shoots, and its brown/orange seed coloration. The plant has a climbing spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKwesflut' may be asexually propagated by cuttings, budding and grafting.

COMPARISON WITH PARENTS

The new rose may be distinguished from its seed parent, 'KORwest' by the following combination of characteristics: whereas 'WEKwesflut' usually bears its flower in large clusters, 'KORwest' bears its flower singly or in significantly smaller clusters. The seed parent bears foliage of medium green coloration with little red suffusion on the leaves and the stems, whereas the new variety bears foliage of dark olive-green coloration with significantly more red suffusion on the leaves and the stems.

The new variety may be distinguished from its pollen parent, 'WEKplasol' by the following combination of characteristics: whereas 'WEKwesflut' bears double flowers (about 21 to 30 petals), average in size (about 7.3 to about 10.3 cm. in diameter) and of apricot orange coloration with a yellow reverse, 'WEKplasol' bears single flowers (about 5 petals) of significantly smaller size (about 6 to about 7 cm. in diameter) and of yellow coloration that blushes as the flower ages. The new variety bears an moderately rough peduncle with numerous stipitate glands that bear the sweet juniper fragrance of moss roses, whereas the pollen parent bears an almost entirely smooth peduncle with very few odorless stipitate glands.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of November. Phenotypic expression may vary with environmental, cultural and climatic conditions, as well as differences in conditions of light and soil.

Botanical designation: The new variety botanical designation is *Rosa hybrida* cv. 'WEKwesflut'.

FLOWER

The new variety rarely bears its flowers singly, usually in clusters of four or more per stem. Flowers may be borne in regular rounded clusters on strong somewhat short to medium length stems (about 35 to about 80 cm.). Outdoors, the plant blooms abundantly and nearly continuously during the growing season. The flowers have a strong spicy fragrance.

BUD

The peduncle is about 3.0 to about 6.5 cm. in length, of average caliper (about 0.15 to about 0.3 cm. in diameter), usually erect and very stiff. It is very rough, with numerous stipitate glands that bear the strong moss-rose fragrance of sweet juniper. Peduncle color is between 144B and 147C often heavily suffused, especially on the side exposed to the sun. The intensity of the red suffusion darkens with the age of the flower. At the bud stage, the suffusion is between 185A and 183B gradually darkening to between 187B and 183B on a fresh open flower. On a three-day-old flower, the suffusion on the peduncle intensifies further to between 187A and 183A.

Before the calyx breaks, the bud is about 1.0 to about 1.5 cm. in diameter at the widest point, about 1.0 to about 1.9 cm. in length, and moderately pointed to somewhat ovoid in shape. The surface of the bud bears few foliaceous appendages and some stipitate glands, usually with slender entire foliaceous parts extending beyond the tip of the bud about ¼ or more of its length. Bud color is between 144A and 147B often heavily suffused, especially on the side exposed to the sun, to as dark as between 187A and 183A.

The sepals are about 1.9 to about 2.7 cm. in length and about 0.7 to about 1.1 cm. in width at the widest point. The outer surface color of the sepal is between 144A and 147B often heavily suffused, especially on the side exposed to the sun, to as dark as between 187A and 183A. The inner surface color of the sepal is between 145B and 137C and covered with fine wooly tomentum; sepal margins are lined with numerous stipitate glands and hairs. As the flower ages, a red suffusion of between 185C and 187D appears at the base and center of the inner surface.

As the petals open (after the calyx breaks), the bud is about 1.6 to about 2.3 cm. in diameter at the widest point, about 1.9 to about 2.4 cm. in length, and ovoid to somewhat pointed in form. The color of the under surfaces of the newly opened petals is between 24C and 32B usually blushed on the outermost petals with as dark as between 187B and 46A. At the point where the petal attaches, there is a moderately large zone of near 7D. On the upper surfaces of the newly opened petals, at the point where the petal attaches, there is a very large zone of between 9B and 12B that gradually suffuses at about one-third to half of the petal length to as dark as between 32A and 33A.

BLOOM

When fully open, the bloom ranges from about 7.3 to about 10.3 cm. in diameter. Petalage is double with about 21 to 30 petals and about 2 to 6 petaloids irregularly arranged. When partially open, the bloom form is moderately high centered to slightly cupped, and the petals are somewhat tightly spiraled to slightly cupped with petal edges somewhat reflexed outward. When fully open, the bloom form is cupped, and the petals are more loosely cupped with petal edges slightly reflexed outward and sometimes, especially on the inner petals, very rolled inward.

PETALS

The substance of the petals is somewhat slight and moderately thin, with upper and under surfaces moderately shiny. The outer petals are broadly round in shape with rounded apices, sometimes slightly notched with one to two notches. The inner petals are moderately obovate in shape with rounded apices, sometimes slightly notched with one to two notches. The petals are about 3.8 to about 5.3 cm. in length and about 3.5 to about 5.7 cm. in width at the widest point. Petal margins are entire.

NEWLY OPENED FLOWER

The under surface color of the outer petals is between 18B and 16B sometimes blushed on the outermost petals with as dark as between 187C and 46B. There is little to no visible change in coloration at the point where the petal attaches. On the upper surfaces of the outer petals, at the point where the petal attaches, there is a very large zone of between 12C and 11A that gradually suffuses at about one-third to half of the petal length to as dark as between 41C and 44D.

The under surface color of the intermediate and inner petals is between 18B and 16B. On the upper surfaces of the intermediate and inner petals, at the point where the petal attaches, there is a very large zone of between 12C and 11A that gradually suffuses at about one-third to half of the petal length to as dark as between 43C and 44D.

The general tonality of the newly opened flower consists of a very large central zone of between 12C and 11A that gradually suffuses at about one-third to half of the petal length to as dark as between 43C and 44D.

THREE-DAY-OLD FLOWER

The under surface color of the outer and inner petals is between 20D and 27B sometimes blushed on the outermost petals with between 187D and 46C. On the upper surfaces of the outer and inner petals, at the point where the petal attaches, there is a very large zone of between 8C and 10B that gradually suffuses at about one-third to half of the petal length to as dark as between 41C and 52C.

The general tonality of the three-day-old flower consists of a very large central zone of between 8C and 10B that gradually suffuses at about one-third to half of the petal length to as dark as between 41C and 52C.

On the spent bloom, the petals usually drop off cleanly.

In November in Upland, Calif., blooms on the bush growing outdoors generally last about three to four or more days. Cut roses from plants grown outdoors and kept at normal indoor living temperatures generally last about two to three or more days.

MALE REPRODUCTIVE ORGANS

Stamens are many in number (average about 152) and are arranged regularly about the pistils; a few are mixed with petaloids. The filaments are of medium length (about 0.4 to about 0.6 cm.), most with anthers. Filaments are between 13B and 12A at the base suffusing to between 30B and 34A in color near the top. The anthers are of medium size for the class and all open approximately at the same time. Anther color is between 15A and 16A when immature and between 163C and 200A at maturity. Pollen is very abundant.

FEMALE REPRODUCTIVE ORGANS

Pistils vary in number (average about 107). The styles are moderately uneven, average in length (about 0.4 to about 0.6 cm.), very thin in caliper, and moderately loosely bunched. Stigma color is near 16B. Style color is between 1D and 2D lightly suffused near the top with near 53B. Ovaries are usually all enclosed in the calyx.

Hips are of average length (about 1.1 to about 1.6 cm.), very rounded to moderately globular in form, and between 28A and 30B in color when ripe. The hip surface is very smooth with thick fleshy walls. The sepals are moderately permanent. The seeds are irregularly rounded, smooth in texture, approximately 8 to about 21 per hip, 0.3 to about 0.4 cm. in diameter at the widest point and between 167C and 164B in color.

FOLIAGE

The compound leaves are usually comprised of three to five or more leaflets and are borne abundantly. The five-leaflet leaves are about 9.7 to about 13.6 cm. in length and about 7.6 to about 11.2 cm. in width at the widest point, very heavy to leathery to slightly crisp in texture, and moderately glossy in finish. The terminal leaflets are about 3.9 to about 6.5 cm. in length and about 2.8 to 4.5 cm. in width at the widest point, shaped oval with acute apices and moderately acute to somewhat rounded bases. Their margins are usually simply serrate.

The upper surface color of the mature leaf is between 147A and 146B sometimes lightly suffused on the midrib with between 187B and 187A. The under surface color of the mature leaf is between 146B and 148A sometimes lightly suffused on the midrib with between 187D and 187C. The upper surface color of the young leaf is between 146A and 146B, usually moderately suffused toward the edge of the leaf and on the midrib with between 187A and 187B. The under surface color of the young leaf is near 146B, usually moderately suffused toward the edge of the leaf with between 187B and 187A and with between 187C to 187B on the midrib.

The rachis is average in caliper and usually smooth but sometimes with one to two small prickles. The upper side is shallowly grooved with few hairs and few stipitate glands on the edges of the grooves. The under side of the rachis is usually smooth with sometimes few small prickles. The rachis color is between 144B and 145A. The upper side is often heavily suffused with between 187A and 187B, especially on the young leaves.

The stipules are about 1.1 to about 2.0 cm. in length and moderately wide (about 0.5 to about 0.8 cm.) with medium straight points that usually turn out at an angle of more than 45 degrees and sometimes recurve toward the stem. The stipules color is between 146B and 144B sometimes lightly suffused on the mature leaves with between 187C and 187D and often moderately suffused on the young leaves with between 187A and 187B.

The petiole is about 0.6 to about 2.1 cm. in length and about 0.1 to about 0.2 cm in diameter at the widest point. The petiole color is between 144B and 145A.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a climbing and spreading tall growing habit (producing canes of about 280 to about 410 cm. in length), with full branching. It displays moderately vigorous growth and the canes are of medium to somewhat heavy caliper for the class.

The color of the major stems is between 146C and 152B. They bear some large prickles that are about 0.5 to about 1.0 cm. in length. The large prickles are almost straight to slightly hooked downward with a medium length narrow oval base; prickle color is between 166B and 166C. The major stem bears no small prickles.

The color of the branches is between 144B and 146C sometimes lightly suffused, especially on the side facing the sun, with between 187D and 183D. They bear few large prickles which are of similar size and shape to the large prickles on the major stems; prickle color is between 183D and 187C. The branches bear no small prickles.

The color of the new shoots is between 144A and 146B usually heavily suffused with between 187A and 187B. They bear some large prickles which are of similar size and shape to the large prickles on the major stems; prickle color is between 187A and 187B. The shoots bear no small prickles.

I claim:

1. A new and distinct Climbing rose plant of the variety substantially as described and illustrated herein.

* * * * *

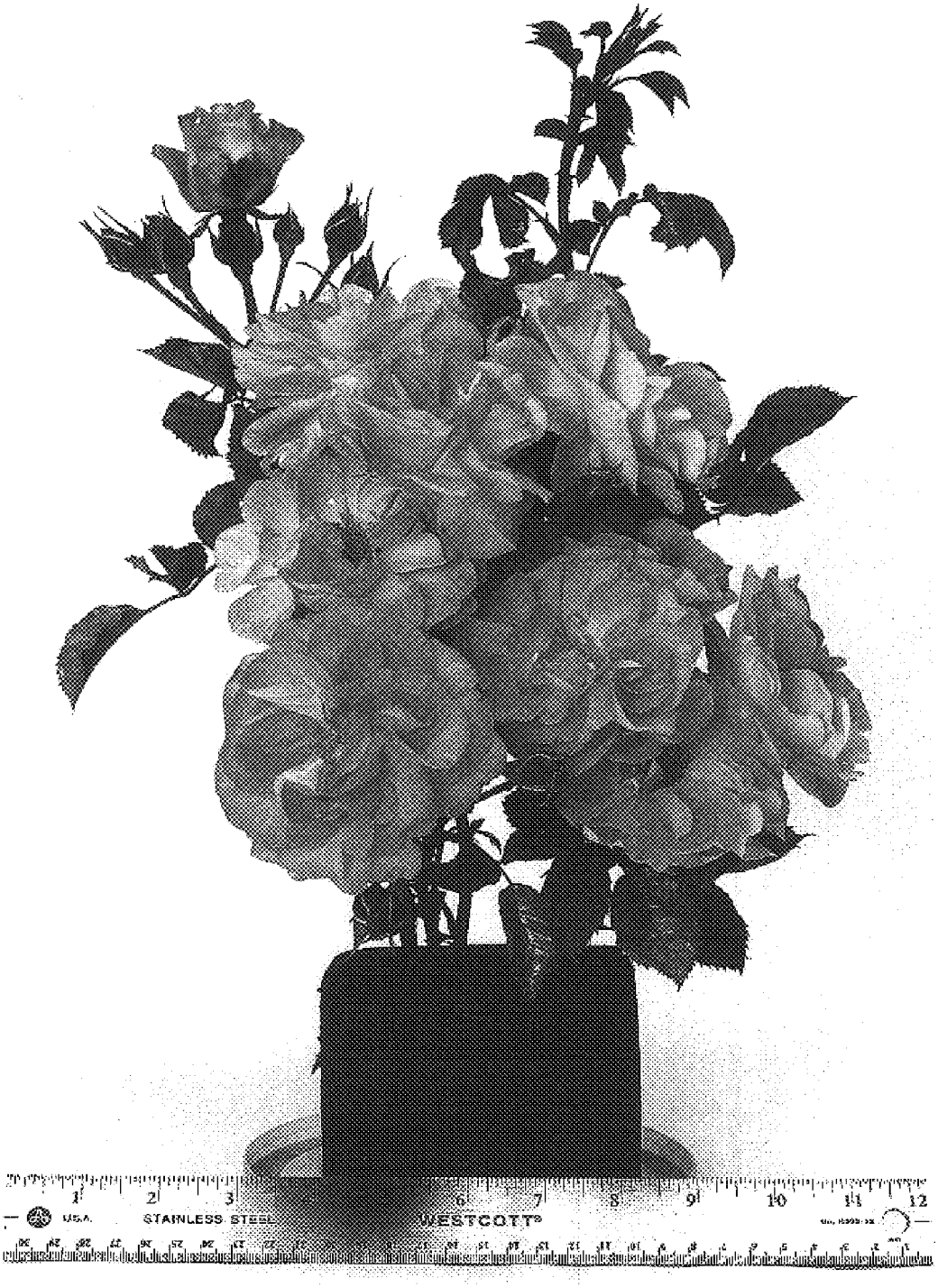
1
2
3
6
7
8
9
10
11
12
USA
STAINLESS STEEL
WESTCOTT